United States Patent [19]
Marshall

[11] Patent Number: 4,848,138
[45] Date of Patent: Jul. 18, 1989

[54] WINDOW GAS MONITOR

[76] Inventor: John M. Marshall, 202 S. Michigan St., South Bend, Ind. 46601

[21] Appl. No.: 219,239

[22] Filed: Jul. 15, 1988

[51] Int. Cl.⁴ ............................................. G01M 3/20
[52] U.S. Cl. ........................................ 73/40.7; 73/40; 116/206
[58] Field of Search ................ 73/40.7, 49.3, 40, 49.8; 116/206, 264

[56] References Cited

U.S. PATENT DOCUMENTS 2,854,815  10/1958  Piquerez .......................... 116/206 X

FOREIGN PATENT DOCUMENTS 3118060  11/1982  Fed. Rep. of Germany ...... 116/206
2176300  12/1986  United Kingdom ................. 73/49.3

Primary Examiner—Stewart J. Levy
Assistant Examiner—Joseph W. Roskos
Attorney, Agent, or Firm—James D. Hall; Todd A. Dawson; Thomas J. Dodd

[57] ABSTRACT

A gas monitor for detecting the presence of absence of a noble gas in the space between two window glazing panels. The monitor is preferably non-reactive with the noble gas, but reactive in a visible way with ambient air. When the noble gas leaks out of the space between the glazing panels and ambient air infiltrates, the monitor provides a visual indicator of the occurrence.

9 Claims, 1 Drawing Sheet

WINDOW GAS MONITOR

SUMMARY OF THE INVENTION

This invention relates to gas monitors, and will have special application to a gas monitor for sensing the presence of a noble gas between the panes of a multiple pane window.

Double or triple paned windows have become extremely popular items for both residential homes and office buildings because of their excellent insulative properties. The space between the panes is referred to in the trade as "dead air" and is often filled with a noble gas such as argon or krypton.

Problems arise when the seal about the window which traps the noble gas between the panes deteriorates or is defective. In such cases, the noble gas leaks out from between the panels which allows air transfer and resultant loss of insulative properties. Since noble gases are colorless, a slow leak in the window may go undetected for some time, and large amounts of energy wasted due to the ineffective insulation.

This invention provides for a monitor to be placed in the space between the window panes. The monitor may take any one of several forms, such as a thin strip, a small bag of crystals, a liquid container, or any other acceptable form which is easily reviewed, but which does not detract from the aesthetic appearance of the window. The monitor is preferably formed from a material which exhibits two distinct chemical properties: it must be non-reactive with the noble gas contained in the space between the windows; and it must react with ambient air in such a way that the reaction is easily observed; i.e., a change in color, crystal structure, phase, etc., by the naked eye.

Accordingly, it is an object of this invention to provide for a monitor which detects the presence of absence of a noble gas in a double or triple paned window.

Another object is to provide for a window gas monitor which is easily read, but which does not detract from the aesthetic appearance of the window.

Another object is to provide for a window gas monitor which is easily installed, is economical, and is highly efficient in detecting gas leaks.

DESCRIPTION OF THE PREFERRED EMBODIMENT

Figure 3:
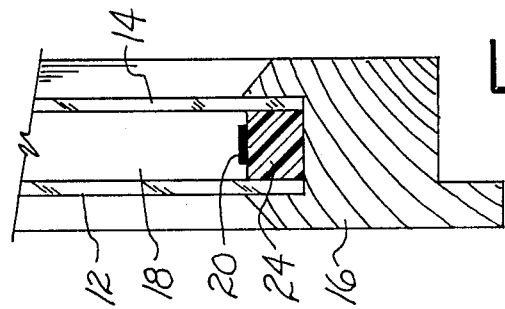
FIG. 3 is a detail view of the gas monitor in a gas leak condition reacting with the infiltrating ambient air.

The preferred embodiments herein disclosed are not intended to be exhaustive or to limit the invention to the precise forms disclosed. They are chosen and described to explain the principles of the invention and their application and practical use to enable others skilled in the art to utilize the inventive concept.

Referring first to the drawings, reference numeral 10 generally indicates a window having dual spaced glazing panels 12, 14 fixed in a sash frame 16. It is understood that this invention is usable in any window arrangement which has two or more spaced glazing panels, regardless of the type of style of window.

Normally, the space 18 defined between glazing panels 12, 14 is pressurized with a colorless inert gas such as argon or krypton. The space 18 with panels 12, 14 forms an insulative barrier which effectively seals the window 10 against air transfer and heat loss through the glazing panels. The insert gas is sealed within space 18 by conventional window sealants such as caulk or the like which serve to seal the glazing panels 12, 14 to sash frame 16.

Figure 2:
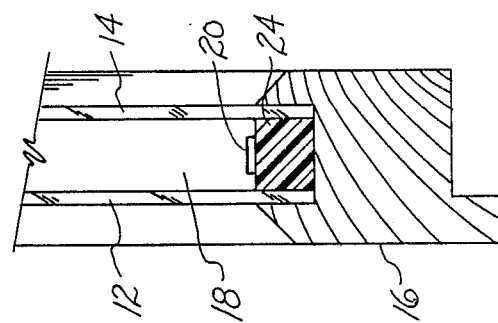
FIG. 2 is a detail view of the gas monitor as seen in a normal condition.
Figure 1:
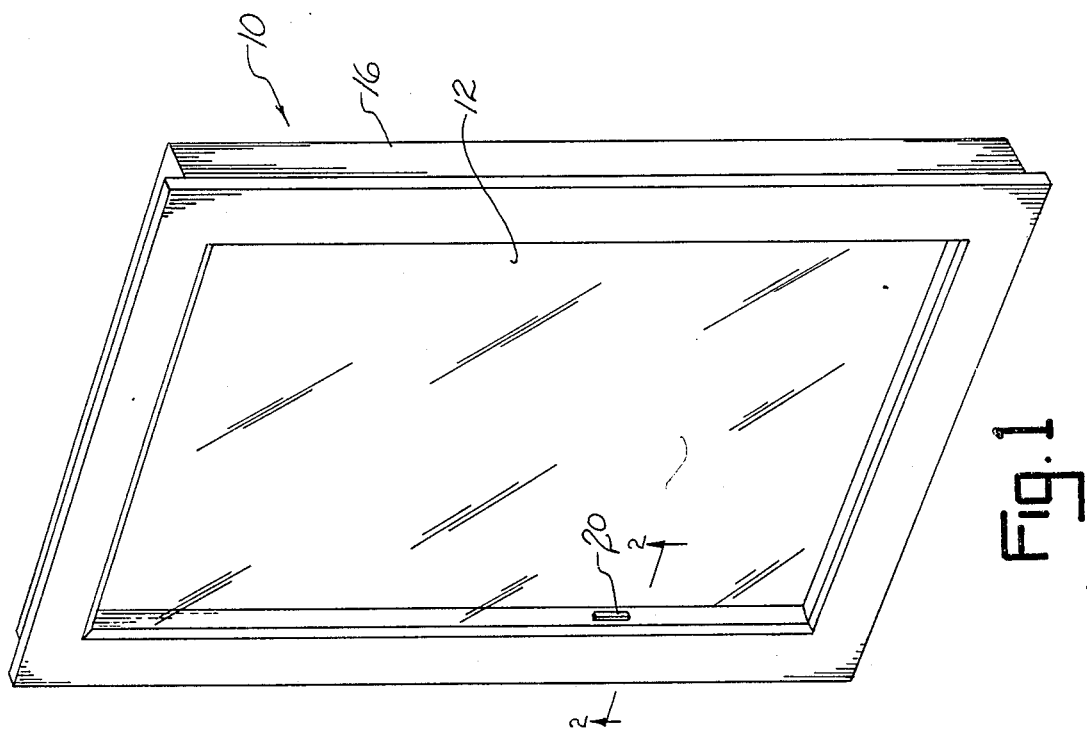
FIG. 1 is a perspective view of a double pane window utilizing the gas monitor of this invention.

Monitor 20, shown in FIGS. 2-3 as strip of lithium metal, is placed between glazing panels 12, 14 and secured to either the sash frame interior 22 or to a glazing panel divider 24. Other examples of some possible compounds for use as a gas monitor are outlined in the examples below. It should be kept in mind that any substance which exhibits non-reactance with noble gases together with a reactance with oxygen, nitrogen, water vapor, or carbon dioxide which can be visually observed may be utilized as a gas monitor within the purview of the invention. The most efficient metals in this regard are the alkali metals and the alkaline earth metals.

In operation, monitor 20 is positioned between panels 12, 14 after all ambient air has been evacuated from space 18. Space 18 is then filled with the preferred noble gas and sealed in a conventional manner. In the embodiment shown in the drawing, the lithium strip monitor 20 is initially very shiny on its surface as shown in FIG. 2. If the noble gas should leak out from space 18, ambient air will infiltrate the space, and lithium strip monitor 20 will rapidly oxidize to a dull black surface finish which is easily observed as shown in FIG. 3.

The following examples of monitor 20 are also submitted for illustrative purposes, but are not intended to limit the invention to any particular monitor.

EXAMPLES 1-5

A hygroscopic compound was placed in a space between two sealed glazing panels and the results observed as a noble gas was first introduced into the space and then allowed to leak out and be replaced by ambient air which included water vapor. The following results were observed with (1) Silica gel - cobalt chloride crystals; (2) Calcium carbonate crystals; (3) Cobalt iodide crystals; and (4) Copper (II) chloride crystals as the monitor.

1—Colorless Silica gel treated with cobalt chloride colorless crystals turned blue within seconds after noble gas evacuation.
2—Colorless calcium carbonate crystals liquefied upon exposure to ambient air.
3—Black cobalt iodide ($CoI_2$) crystals turned green upon exposure to ambient air.
4—$CoI_2$ crystals became brownish-red after extended exposure to ambient air.
5—Brownish-yellow $CuCl_2$ crystals turned green upon exposure to ambient air.

EXAMPLES 6-12

A metal strip was placed in the space between the glazing panels as above described and the results observed when the noble gas was evacuated. The following results with metal strips were observed 6-9—Silver, titanium and lithium changed from shiny to a dull black upon exposure to air.
10—Copper changed from reddish brown to dark brownish black upon exposure to air.

11—Calcium changed from silvery to white upon exposure to nitrogen in the air.

12—Sodium changed from silvery to gray upon exposure to air.

EXAMPLE 13

Bromine liquid is enclosed in a capsule which deteriorates upon exposure to ambient air. After evacuation of the noble gas from between the glazing panels, the capsule deteriorated and reddish-brown bromine vapors escaped and were visible between the glazing panels. It is probable that this result could also be achieved with other volatile colored liquids or with volatile gases such as neon.

I claim:

1. In combination, a window including two or more space glazing panels defining a space therebetween, said glazing panels secured to a window frame so as to seal said space against intrusion of outside air, an inert gas substantially filling the space between said glazing panels, and a gas monitor positioned in said space, said monitor comprising a member which is chemically non-reactive with said inert gas and assumes a first state when positioned in said space, said member chemically reactive with at least major element of outside air wherein leakage of said inert gas and corresponding displacement by said outside air causes said member to virtually immediately assume a second state visibly distinct from said first state whereby leakage of the inert gas from said space is readily detectable.

2. The combination of claim 1 wherein said member includes a strip of metal which oxidizes when exposed to said outside air.

3. The combination of claim 2 wherein said metal strip is selected from the group of materials which consists of silver, titanium, lithium, sodium, copper, and calcium.

4. The combination of claim 2 wherein said metal is selected from the group of materials which consists of the alkali metals and the alkaline earth metals.

5. The combination of claim 1 wherein said member includes hygroscopic crystals which change color when exposed to water vapor in said outside air.

6. The combination of claim 5 wherein said crystals are selected from the group of materials which consists of cobalt chloride treated silica gel, calcium carbonate, cobalt iodide, and copper (II) chloride.

7. The combination of claim 1 wherein said member is a capsule which disintegrates upon exposure to said outside air, said capsule containing a colored volatile material.

8. The combination of claim 7 wherein said colored volatile material is selected from the group of materials which consists of bromine and neon.

9. The combination of claim 1 wherein said member is reactive with very small quantities of one of said major outside air elements.

* * * * *